(12) United States Patent
Seo et al.

(10) Patent No.: US 7,864,643 B2
(45) Date of Patent: *Jan. 4, 2011

(54) APPARATUS AND METHOD FOR TESTING MECHANICAL ENDURANCE OF SURFACE OF OPTICAL DISC, THE OPTICAL DISC OF SAME KIND AS THE TESTED OPTICAL DISC

(75) Inventors: Hun Seo, Yongin-si (KR); Jin Hong Kim, Gyeonggi-do (KR); Seung Yoon Lee, Seoul (KR); Jin Yong Kim, Seongnam-si (KR)

(73) Assignee: LG Electronics Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/520,629

(22) Filed: Sep. 14, 2006

(65) Prior Publication Data
US 2007/0008841 A1    Jan. 11, 2007

Related U.S. Application Data

(62) Division of application No. 10/940,928, filed on Sep. 15, 2004, now Pat. No. 7,626,904.

(30) Foreign Application Priority Data
Sep. 15, 2003    (KR) .................. 10-2003-0064034

(51) Int. Cl.
G11B 20/18    (2006.01)
(52) U.S. Cl. .................... 369/53.13; 369/53.34
(58) Field of Classification Search ............ None
See application file for complete search history.

(56) References Cited

U.S. PATENT DOCUMENTS 4,399,192 A * 8/1983 Russell ............ 428/412
4,410,978 A   10/1983 Van Den Broek et al.
4,681,834 A   7/1987 Simmons, III
4,958,511 A   9/1990 Marcus (Continued)

FOREIGN PATENT DOCUMENTS

GB    438544 A    11/1935

(Continued)

OTHER PUBLICATIONS

International Search Report dated Nov. 26, 2004.

(Continued)

*Primary Examiner*—Christopher R Lamb
(74) *Attorney, Agent, or Firm*—Harness, Dickey & Pierce, P.L.C.

(57) ABSTRACT

An apparatus and method for testing mechanical endurance of a surface of an optical disc is disclosed, which includes a rotating plate on which the optical disc is fixed to generate scratch thereon, and rotating the fixed optical disc; and a plurality of abrasion wheels disposed in perpendicular to the rotating plate, and being in contact with the surface of the optical disc, to generate the scratch on the surface of the optical disc, wherein the scratches generate when the optical disc rotates a predetermined turn, e.g. below ten turns for applying a predetermined load generated from the abrasion wheel on the optical disc.

19 Claims, 6 Drawing Sheets

U.S. PATENT DOCUMENTS

| | | | |
|---|---|---|---|
| 4,966,030 | A | 10/1990 | Kobayashi et al. |
| 5,074,983 | A | 12/1991 | Eltoukhy et al. |
| 5,343,733 | A | 9/1994 | Nakagawa et al. |
| 5,531,095 | A | 7/1996 | Hupf |
| 5,557,039 | A | 9/1996 | Annis et al. |
| 5,568,466 | A | 10/1996 | Komaki et al. |
| 5,615,589 | A | 4/1997 | Roach |
| 5,756,130 | A | 5/1998 | Umebayashi et al. |
| 6,330,820 | B1 | 12/2001 | Cotterill et al. |
| 6,412,330 | B1 | 7/2002 | Dicello et al. |
| 6,502,455 | B1 | 1/2003 | Gitis et al. |
| 6,576,320 | B2 * | 6/2003 | Hayashida et al. ......... 428/64.1 |
| 6,874,350 | B2 | 4/2005 | Seo et al. |
| 7,188,510 | B2 * | 3/2007 | Seo et al. ..................... 73/7 |
| 2002/0054975 | A1 | 5/2002 | Hayashida et al. |
| 2004/0182169 | A1 | 9/2004 | Seo et al. |
| 2004/0226350 | A1 | 11/2004 | Kim et al. |
| 2005/0002286 | A1 | 1/2005 | Yonezawa et al. |
| 2005/0058040 | A1 | 3/2005 | Seo et al. |

FOREIGN PATENT DOCUMENTS

| | | |
|---|---|---|
| JP | 01-143017 | 6/1989 |
| JP | 03-226648 A | 10/1991 |
| JP | 06-201572 | 7/1994 |
| JP | 08-063797 | 3/1996 |
| JP | 08-106663 | 4/1996 |
| JP | 08-233714 | 9/1996 |
| JP | 08-327523 | 12/1996 |
| JP | 10-011953 | 1/1998 |
| JP | 10-261201 | 9/1998 |
| JP | 11-250502 | 9/1999 |
| JP | 2000-28506 A | 1/2000 |
| JP | 2001-91445 | 4/2001 |
| JP | 2002-260280 | 9/2002 |
| JP | 2006-514293 | 4/2006 |
| KR | 1988-0001420 | 8/1988 |
| KR | 2001-0053357 | 6/2001 |
| KR | 2002-0009786 | 2/2002 |
| KR | 2003-0001529 | 1/2003 |

OTHER PUBLICATIONS

KS M ISO 5470-1.
Japanese Office Action dated Jul. 21, 2009 with English translation.
Korean Office Action dated Feb. 18, 2009 with English translation.
Korean Office Action dated Feb. 19, 2009 with English translation.
Notice of Allowance dated Feb. 25, 2010, for counterpart Korean Patent Application No. 9-5-2010-008199981.
Notice of Allowance dated Feb. 25, 2010, for counterpart Korean Patent Application No. 9-5-2010-008200085.
Office Action with English translation dated Feb. 12, 2010 for counterpart Japanese Patent Application No. 2007-205948.

* cited by examiner

APPARATUS AND METHOD FOR TESTING MECHANICAL ENDURANCE OF SURFACE OF OPTICAL DISC, THE OPTICAL DISC OF SAME KIND AS THE TESTED OPTICAL DISC

This application is a divisional of U.S. application Ser. No. 10/940,928, filed Sep. 15, 2004 now U.S. Pat. No. 7,626,904, the entirety of which hereby is incorporated herein by reference.

FOREIGN PRIORITY INFORMATION

This application claims the benefit of Korean Application No. 10-2003-064034, filed on Sep. 16, 2003, the entirety of which hereby is incorporated herein by reference.

BACKGROUND OF THE INVENTION

1. Field of the Invention

The present invention relates to an apparatus and method for testing quality of an optical disc, and more particularly, to an apparatus and method for testing mechanical endurance of a surface of an optical disc, the optical disc of same kind as the test disc.

2. Discussion of the Related Art

Up to now, there are recording media such as a magnetic recording tape, a laser disc (LD) or a compact disc (CD) as an optical disc, and a digital video disc (DVD) newly born with a vast recording capacity.

Since the optical disc among the recording media utilizes a digital recording system different from the conventional recording system, that is, magnetic recording system, and has a very small volume and weight, it is efficient and convenient to keep and carry, so that it is a recent trend for a consumer to prefer the optical disc.

However, even any appliance should be used without any defect, and if there were any problem in quality, the consumer's reliability for the manufacturer would be decreased.

This causes more serious problem in the optical disc having minute signal characteristics and brings inferior quality originated from scratch, deformity, fingerprint, and attachment of foreign material during manufacturing of the product.

Thus, a produced optical disc undergoes the quality test as a next process, and the optical disc is shipped to an optical disc market.

A conventional quality test for an optical disc is generally performed by four measuring drives.

First, on the assumption that the characteristics of optical discs manufactured by the same equipment are identical, the manufacturer makes a choice of an arbitrary optical disc from all of the manufactured optical discs, and loads the selected optical disc onto a measuring system.

In the first measuring drive, a high frequency wave signal and a jitter are measured by means of a signal reproduced from the optical disc.

In the second measuring drive, a servo signal (a focusing error signal and a tracking error signal) are measured based on a signal reproduced from the optical disc.

In the third measuring drive, the mechanical characteristics of the optical disc, which undergoes the quality test, are measured.

Finally, in the fourth measuring drive, the optical characteristics of the optical disc are measured.

As described above, according to the conventional quality test of the optical disc, an accuracy of information recording, and the mechanical characteristics and the optical characteristics of the optical disc are inspected.

From these, since a mechanical damage that would occur on an incident surface of an information recording/reproducing laser beam during the use of a high density optical disc, that is, a scratch and the like causes the deterioration of a signal of an optical disc as well as data loss, and in more worse case, brings the recording and/or reproducing of information onto the optical disc impossible, the damage takes the most important portion of the quality test of the optical disc.

Accordingly, in order to prevent this problem, a protective coating may be formed to enhance the mechanical stiffness or hardness of the surface of the optical disc.

However, after forming the protective coating on the surface of the optical disc for this purpose, the mechanical characteristics of the protective coating should be quantized. Namely, there is need to quantize for how long the protective coating endure the scratch which would occur during the use of the optical disc.

There are a pencil hardness test and a taber abrasion test as a test for the quantization of surface-proof of the high-density optical disc.

The pencil hardness test is an estimating method for estimating the scratch at a hardness value correspondent to a hardness of the pencil at an instant when the scratch occurs by contacting pencils having different hardness to the optical disc in a rectilinear motion.

However, since the pencil hardness test is a test for generating the scratch by which a human contacts the pencil on the surface of the optical disc, the pencil hardness test has disadvantages in that it is difficult not only to maintain the same load continuously, but also to generate the quantization scratch because the scratch does not occur as many as desired.

The taber abrasion test is a test to estimate the degree of endurance by uniformly wearing the surface of the optical disc while giving a predetermined load by means of D1004 method of a standard, American Society for Testing and Materials (ASTM) as a kind of an abrasion wheel.

In the conventional taber abrasion testing apparatus, if an optical disc to be scratched is loaded and rotated, a plurality of abrasion wheels having a predetermined weight contact the optical disc at a perpendicular position to the optical disc so that scratch the surface of the optical disc by a uniform load for at least ten or more rotations of the optical disc.

At that time, the ASTM defines the load generated from the abrasion wheel less than 9.8N(1000 gf), and there are several kinds such as CS-10F, CS-10, and CS-17 to be used.

The taber abrasion testing apparatus having the aforementioned structure is an equipment designed for the purpose of not testing the mechanical endurance of the surface of the optical disc by scratching the optical disc, but testing the degree of the scratch of general plastic goods.

Therefore, the scratch occurring by the taber abrasion testing apparatus is remarkably different from the scratch generated when the optical disc is used actually in a real life.

Namely, the taber abrasion testing apparatus determines the endurance of the surface of the optical disc by wearing the surface. This is remarkably different from the situation that real-generated scratch is reacted in a drive (for example, an optical disc drive) for driving the optical disc by responding the operation.

Therefore, since the manufacturer determines the quality of the optical disc by his relative determination with his veteran know-how not quantitative classification according to an actual reference standard when to determine the quality of the optical disc poor or good by the taber abrasion testing apparatus, there are a plenty of errors. Moreover, since the scratches generated on the optical disc in the real life and by the taber abrasion testing apparatus are different from each other in the shape, a try to determine the optical disc poor or good with only the know-how without an absolute reference value makes vast errors.

As described above, since, up to now, there is not a special method for quantizing generation degree of the scratch in order to test the mechanical endurance of the surface of the optical disc, a quantization of the degree of the scratch is urgently demanded.

SUMMARY OF THE INVENTION

Accordingly, the present invention is directed to an apparatus and method for testing mechanical endurance of a surface of an optical disc that substantially obviates one or more problems due to limitations and disadvantages of the related art.

An object of the present invention is to provide an apparatus and method for testing mechanical endurance of a surface of an optical disc, to enhance the mechanical characteristics of the surface of the optical disc by quantizing the characteristics of the mechanical endurance.

Another object of the present invention is to provide an apparatus and method for testing mechanical endurance of a surface of an optical disc, to improve reliability and decrease a testing cost.

Another object of the present invention is to provide an apparatus and method for testing mechanical endurance of a surface of an optical disc, to test and determine the quality of an optical disc as a good or poor one with rapidness and accuracy by setting a realizable absolute reference value.

Another object of the present invention is to provide an apparatus and method for testing mechanical endurance of a surface of an optical disc, to improve reliability in testing the mechanical endurance of the surface of the optical disc by generating a scratch having a similar type to that of a scratch generated in a real life.

Another object of the present invention is to provide an apparatus and method for testing mechanical endurance of a surface of an optical disc, to improve reliability in testing the mechanical endurance of the surface of the optical disc such as BD-RE (Blu-ray Disc-REwritable) and BD-WO (Blu-ray Disc-Write Once) which records information after generating a scratch on the surface of the optical disc.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an apparatus for a scratch endurance of a surface of an optical disc includes a rotating plate, on which an optical disc is loaded and rotating the optical disc, and a plurality of abrasion wheels being in contact with the surface of the optical disc, to generate a scratch on the surface of the optical disc, the being generated during the optical disc rotates a predetermined turns while the abrasion wheels apply a predetermined load on the optical disc, wherein the apparatus determines whether the optical disc has a predetermined endurance by comparing a jitter value from the scratch generated on the surface of the optical disc with a predetermined jitter value.

Herein, the optical disc is formed of any one of BD-RE (Blu-ray Disc-REwritable), BD-WO (Blu-ray Disc-Write Once), and BD-RO (Blu-ray Disc-Read Only).

Also, the load of the abrasion wheel, applied on the optical disc, is in a range between 0.49N(50 gf) and 7.35N(750 gf).

Also, the scratch generated on the surface of the optical disc has a depth between 0 μm and 2 μm, and the abrasion wheel is any one of CS-10F, CS-10, and CS-17.

Herein, the scratch generates when the optical disc rotates a predetermined turn, e.g. below ten turns, during applying the load of 0.49N(50 gf) to 2.45N(250 gf) on the surface of the optical disc with the abrasion wheel of CS-10F. Or, the scratch generates when the optical disc rotates below ten turns during applying the load of 1.47N(150 gf) to 4.41N(450 gf) on the surface of the optical disc with the abrasion wheel of CS-10. Or, the scratch generates when the optical disc rotates below ten turns during applying the load of 2.45N(250 gf) to 7.35N(750 gf) on the surface of the optical disc with the abrasion wheel of CS-17.

In another aspect of the present invention, a method for testing a scratch endurance of a surface of an optical disc includes the steps of contacting a plurality of abrasion wheels with a predetermined load to the surface of the optical disc, maintaining the contact between the optical disc and the abrasion wheels until the optical disc rotates a predetermined turns, and determining whether the optical disc has a predetermined endurance by measuring a jitter value obtained from a signal of reproducing information recorded on the optical disc.

In another aspect of the present invention, a method of testing a scratch endurance of a surface of an optical disc includes the steps of contacting a plurality of abrasion wheels with a predetermined load to the surface of the optical disc to generate a scratch on the surface of the optical disc, comparing a jitter value obtained from a signal of reproducing information recorded on the optical disc with a predetermined jitter value, and determining whether the optical disc has a predetermined endurance based on a result of the comparing step.

In another aspect of the present invention, an optical disc, the optical disc is made by the same manufacturing process as the tested optical disc In another aspect of the present invention, an information recording medium having an entrance surface, which has a sufficient resistance or not with respect to a scratch, the information recording medium can be verified or is the same kind of the disc verified by a test to determine whether the surface of the information recording medium has a sufficient resistance, wherein the test includes the steps of contacting a plurality of abrasion wheels with a predetermined load to the surface of the information recording medium to generate a scratch on the surface of the information recording medium, comparing a jitter value obtained from a signal of reproducing information recorded on the information recording medium with a predetermined jitter value, and determining whether the information recording medium has a predetermined endurance based on a result of the comparison.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
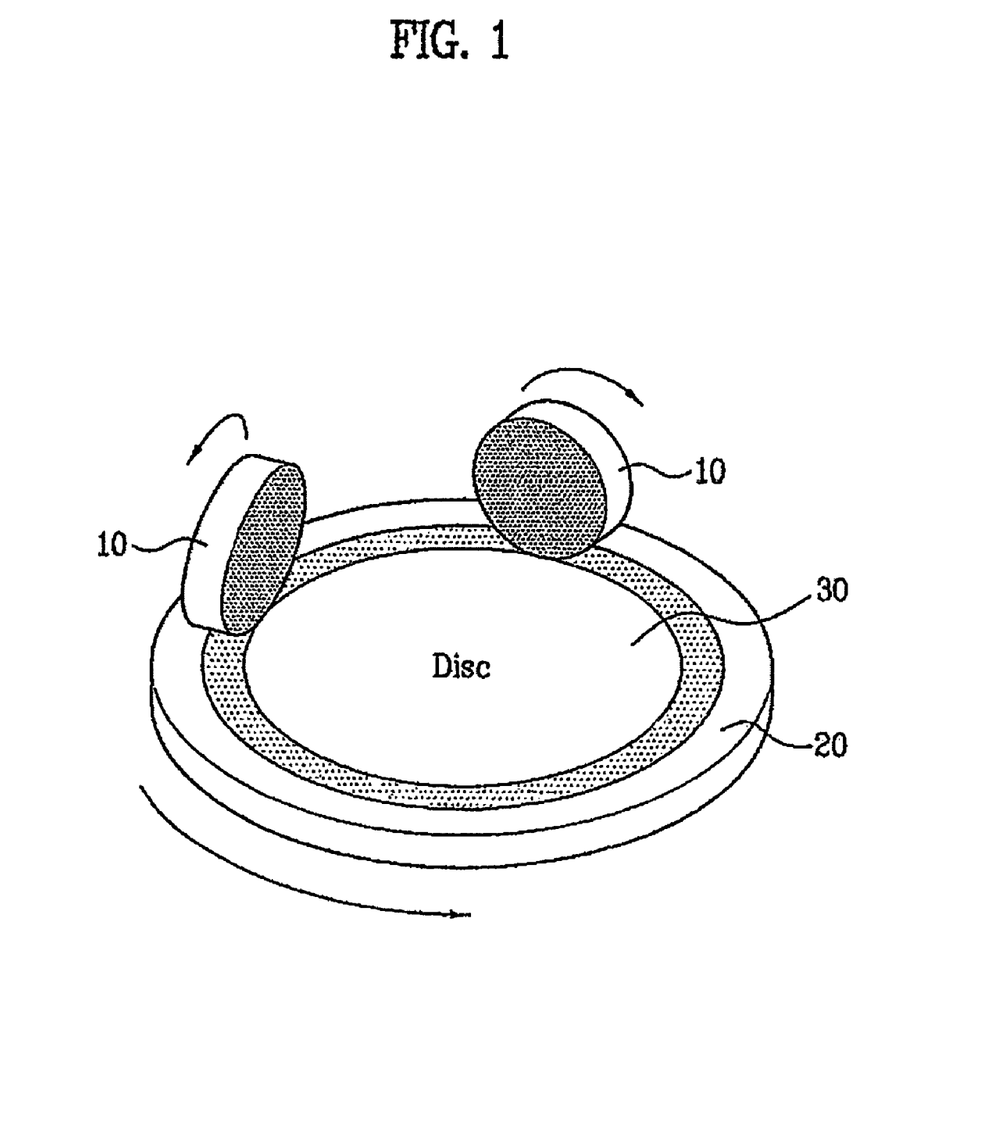
FIG. 1 illustrates a schematic view showing a taber abrasion testing apparatus according to the present invention.

FIG. 1 illustrates a schematic view showing a taber abrasion testing apparatus according to the present invention.

As described in FIG. 1, an apparatus for testing mechanical endurance of a surface of an optical disc includes a rotating plate 20, and a plurality of abrasion wheels 10. On the rotating plate 20, an optical disc 30 to be scratched is loaded, for rotation of the loaded optical disc 30. Also, the plurality of abrasion wheels 10 are disposed in perpendicular to the rotating plate 20, for the contact with the optical disc 30, and generation of scratches on the surface of the optical disc 30.

The abrasion wheels contacted with the optical disc are also rotated to a direction according to the rotation of the optical disc, one wheel being rotated to reverse direction with respect to the other abrasion wheel.

In this state, the scratches generate when the optical disc 30 rotates a predetermined turn, e.g. below ten turns for applying a predetermined load generated from the abrasion wheel 10 on the optical disc 30.

The optical disc 30 may be BD-RE (Blu-ray Disc-REwritable), BD-WO (Blu-ray Disc-Write Once), or BD-RO (Blu-ray Disc-Read Only).

That is, the optical disc 30 may be used of any one of an optical disc on which no information is recorded, an optical disc on which information is recorded one time, and an optical disc on which information is recorded more than one time.

Also, it is preferable to maintain the load generated from the abrasion wheel 10, applied on the optical disc 30, between 0.49N(50 gf) and 7.35N(750 gf).

In this case, the scratch generated on the surface of the optical disc 30 may have a depth between 0 μm and 2 μm.

Also, the abrasion wheel 10 may be used of any one of CS-10F, CS-10, and CS-17.

Under the condition of using the abrasion wheel of CS-10F in the present invention, the load between 0.49N(50 gf) and 2.45N(250 gf) is applied on the optical disc, and the optical disc rotates below ten turns, so that the scratch generates on the surface of the optical disc.

Under the condition of using the abrasion wheel of CS-10 in the present invention, the load between 1.47N(150 gf) and 4.41N(450 gf) is applied on the optical disc, and the optical disc rotates below ten turns, so that the scratch generates on the surface of the optical disc.

Under the condition of using the abrasion wheel of CS-17 in the present invention, the load between 2.45N(250 gf) and 7.35N(750 gf) is applied on the optical disc, and the optical disc rotates below ten turns, so that the scratch generates on the surface of the optical disc.

A method for testing mechanical endurance of the surface of the optical disc according to the present invention will be described as follows.

Figure 2:
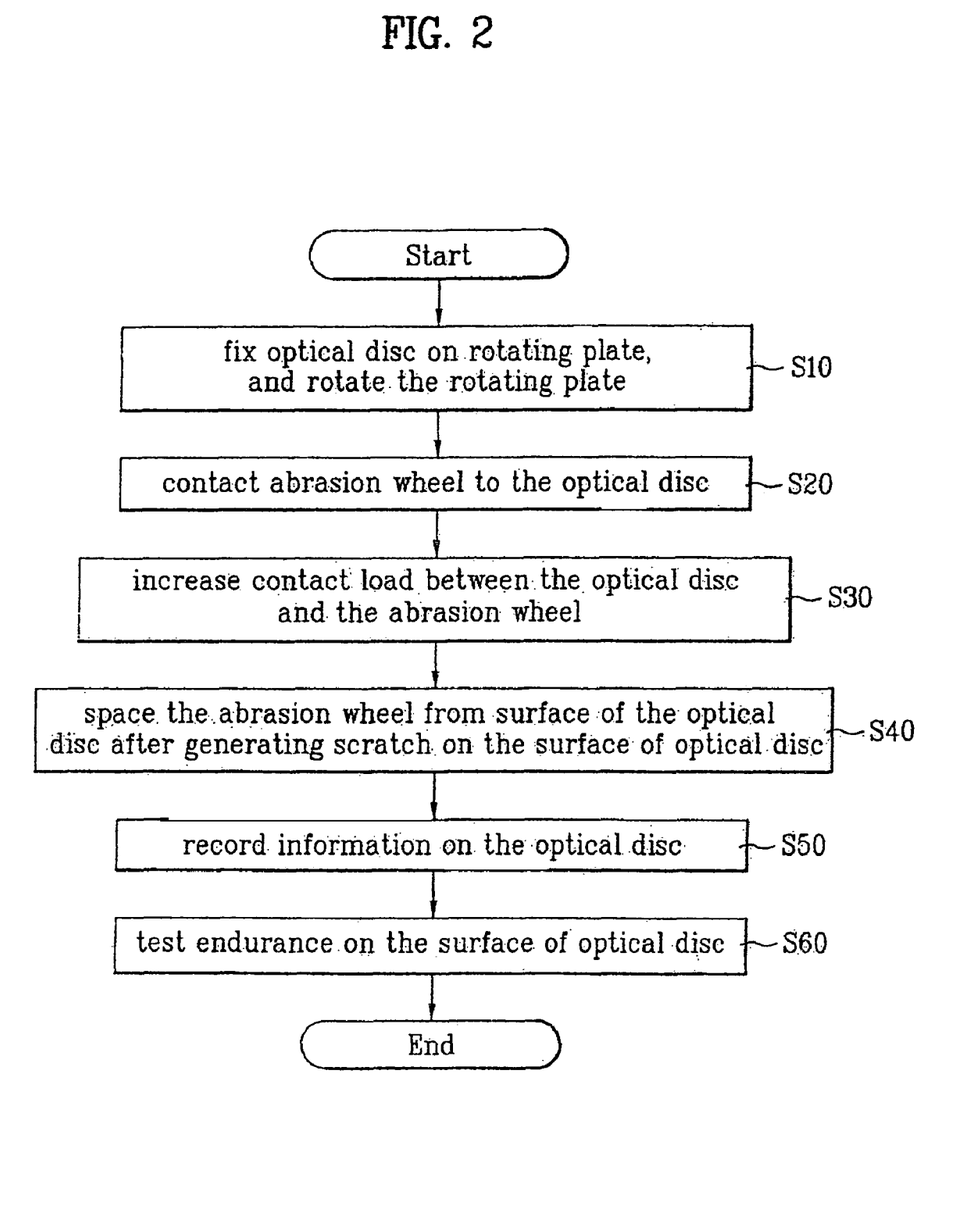
FIG. 2 illustrates a flowchart showing a method of testing mechanical endurance of a surface of an optical disc for BD-WO (Blu-ray Disc-Write Once) according to the present invention.

FIG. 2 illustrates a flowchart showing a method of testing mechanical endurance of a surface of an optical disc for BD-WO (Blu-ray Disc-Write Once) according to the present invention.

Referring to FIG. 2, first, the optical disc is fixed on the rotating plate, and then the rotating plate rotates together with the optical disc (S10).

Subsequently, the abrasion wheel contacts on the surface of the optical disc being rotated (S20), and the contact load between the optical disc and the abrasion wheel is increased to a preset level (S30).

At this time, it is preferable to maintain the load generated from the abrasion wheel, applied on the surface of the optical disc, between 0.49N(50 gf) and 7.35N(750 gf).

Under the condition of using the abrasion wheel of CS-10F, the load between 0.49N(50 gf) and 2.45N(250 gf) is applied on the surface of the optical disc. In case of using the abrasion wheel of CS-10, the load between 1.47N(150 gf) and 4.41N (450 gf) is applied on the surface of the optical disc. In case of using the abrasion wheel of CS-17, the load between 2.45N (250 gf) and 7.35N (750 gf) is applied on the surface of the optical disc.

Next, the contact load between the optical disc and the abrasion wheel is maintained continuously until the optical disc rotates below ten turns, whereby the scratches generate on the surface of the optical disc. Then, the abrasion wheel is spaced apart from the surface of the optical disc (S40).

After that, the testing apparatus records information on the optical disc having the scratches (S50), and determines whether the quality of the optical disc is good or poor by measuring a jitter value from a signal of reproducing the information recorded on the optical disc (S60).

Figure 3:
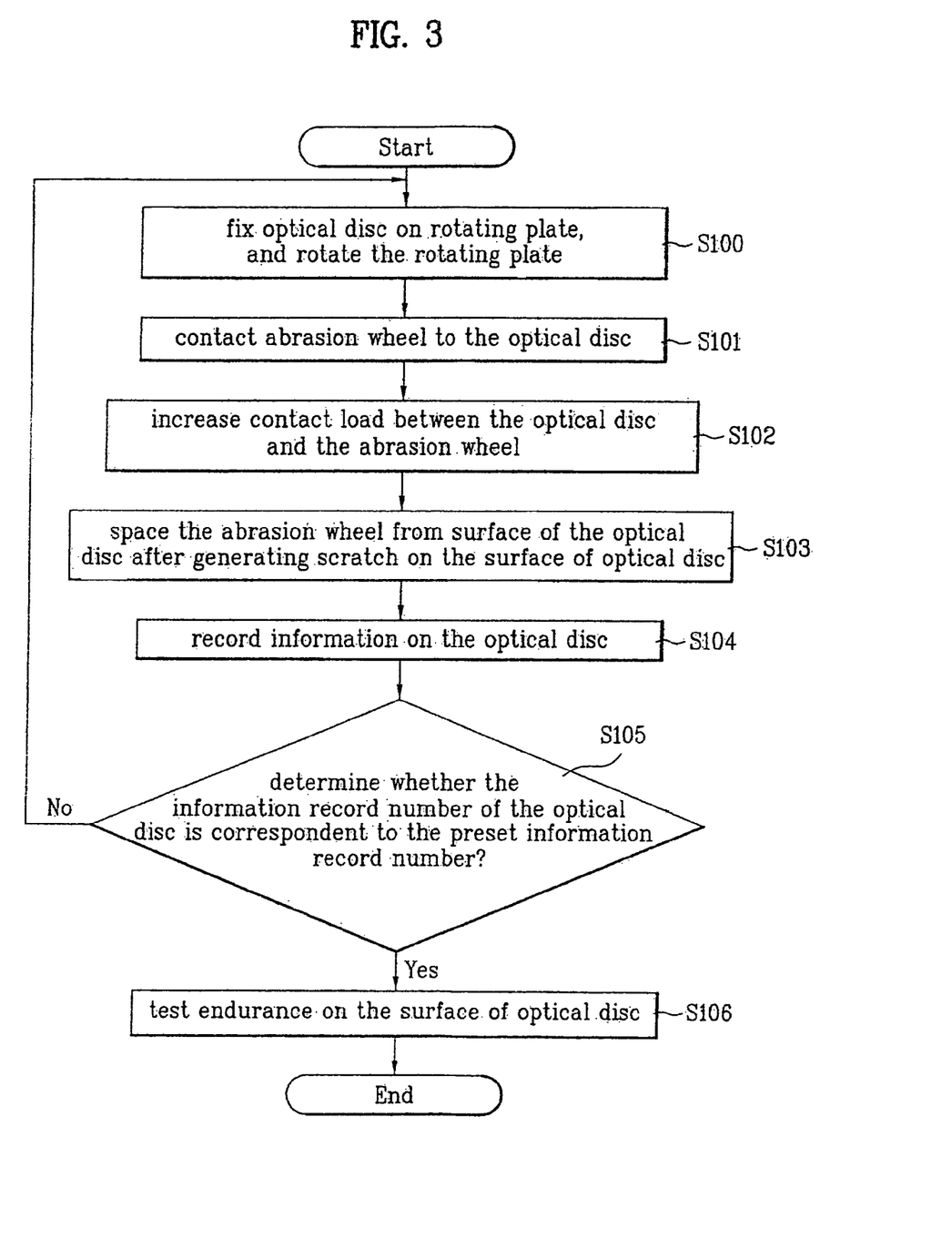
FIG. 3 illustrates a flowchart showing a method of testing mechanical endurance of a surface of an optical disc for BD-RE (Blu-ray Disc-REwritable) according to the present invention.

FIG. 3 illustrates a flowchart showing a method of testing mechanical endurance of a surface of an optical disc for BD-RE (Blu-ray Disc-REwritable) according to the present invention.

As shown in FIG. 3, first, the optical disc is fixed on the rotating plate, and then the rotating plate 20 rotates together with the optical disc (S100).

Subsequently, the abrasion wheel contacts on the surface of the optical disc being rotated (S101), and the contact load between the optical disc and the abrasion wheel is increased to a preset level (S102).

At this time, it is preferable to maintain the load generated from the abrasion wheel, applied on the surface of the optical disc, between 0.49N(50 gf) and 7.35N(750 gf).

Next, the contact load between the optical disc and the abrasion wheel is maintained continuously until the optical disc rotates below ten turns, whereby the scratches generate on the surface of the optical disc. Then, the abrasion wheel 10 is spaced apart from the surface of the optical disc (S103).

Subsequently, the testing apparatus records information on the optical disc having the scratches (S104), and determines whether the information record number of the optical disc is correspondent to the preset information record number (S105).

At this time, the preset information record number may be in a range between 1 and 1000.

If it is determined that the information record number of the optical disc is correspondent to the preset information record number, the testing apparatus determines whether the quality of the optical disc is good or poor by measuring a jitter value from a signal of reproducing the information recorded on the optical disc (S106).

However, if it is determined that the information record number of the optical disc is not correspondent to the preset information record number, the testing apparatus performs again the process step of rotating the optical disc by the rotating plate.

Figure 4:
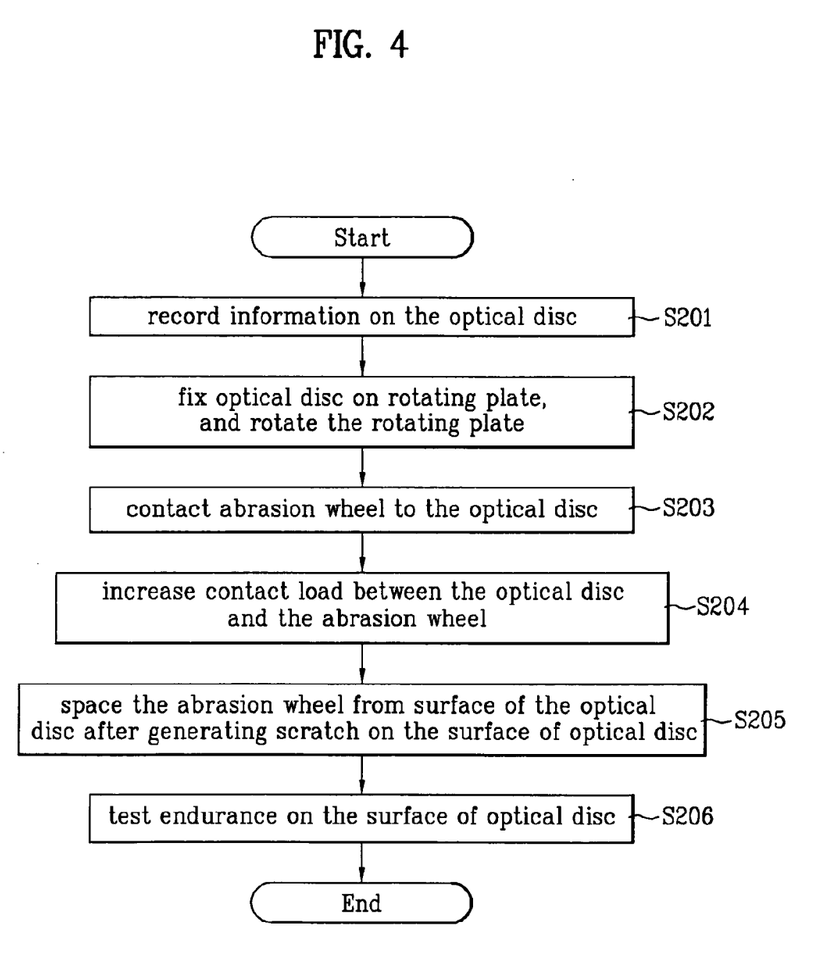
FIG. 4 illustrates a flowchart showing a method of testing mechanical endurance of a surface of an optical disc for BD-RO (Blu-ray Disc Read Only) according to the present invention.

FIG. 4 illustrates a flowchart showing a method of testing mechanical endurance of a surface of an optical disc for BD-RO (Blu-ray Disc Read Only) according to the present invention.

As shown in FIG. 4, first, information is recorded on the optical disc by the testing apparatus (S201).

Subsequently, the testing apparatus fixes the optical disc, on which the information is recorded, to the rotating plate, and then rotates the optical disc by the rotating plate (S202).

After that, the abrasion wheel contacts on the surface of the optical disc being rotated (S203), and the contact load between the optical disc and the abrasion wheel is increased to a preset level (S204).

Herein, it is preferable to maintain the load generated from the abrasion wheel 10, applied on the optical disc 30, between 0.49N(50 gf) and 7.35N(750 gf).

Next, the contact load between the optical disc and the abrasion wheel is maintained continuously until the optical disc rotates below ten turns, whereby the scratches generate on the surface of the optical disc. Then, the abrasion wheel is spaced apart from the surface of the optical disc (S205).

Then, the testing apparatus determines whether the quality of the optical disc is good or poor by measuring a jitter value from a signal of reproducing the information recorded on the optical disc (S206).

Figure 5:
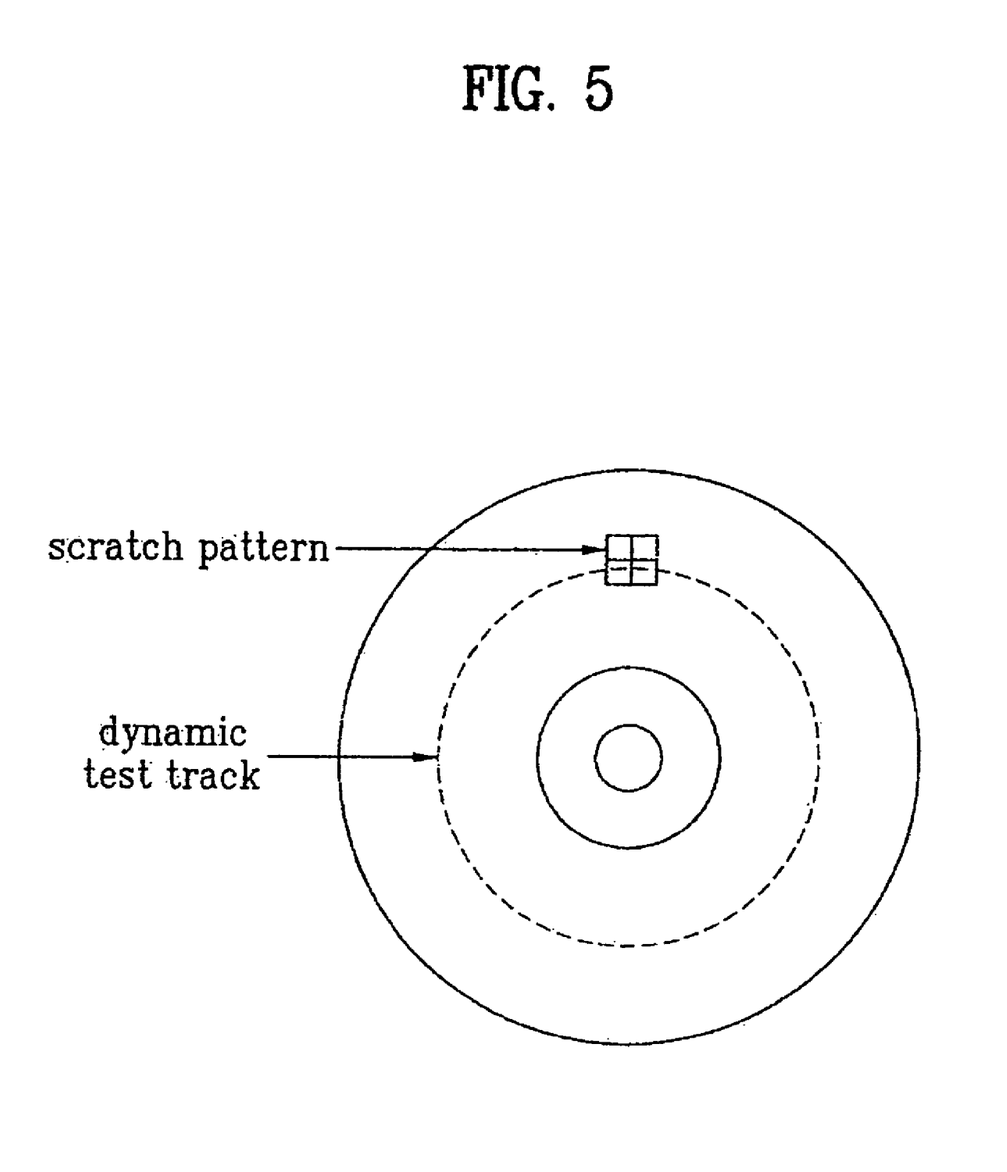
FIG. 5 illustrates a view explaining a predetermined scratch pattern generated on an optical disc by using a microscratch tester according to the present invention.

FIG. 5 illustrates a view explaining a predetermined scratch pattern generated on an optical disc by using a microscratch tester according to the present invention.

Referring to FIG. 5, the testing apparatus according to the present invention maintains the contact load between the optical disc and the abrasion wheel until the optical disc rotates below ten turns, to generate the scratch on the surface of the optical disc.

Figure 6:
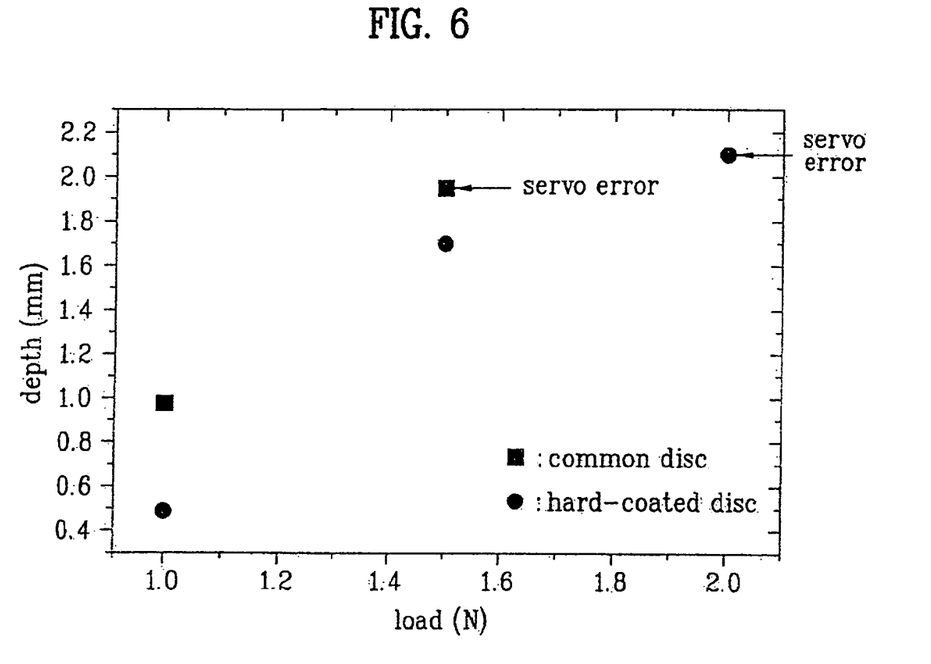
FIG. 6 illustrates a graph showing a scratch depth depending on a load of an abrasion wheel applied on an optical disc according to the present invention.

FIG. 6 illustrates a graph showing a scratch depth depending on a load of an abrasion wheel applied on an optical disc according to the present invention.

FIG. 6 is a graph of comparing a bare disc having no coating layer thereon with a hard-coated disc having a coating layer thereon.

As shown in FIG. 6, when generating the scratch having a depth of 2 μm or more, servo errors of the bare disc having no coating layer and the hard-coated disc having the coating layer are observed.

That is, when performing the test for endurance of the surface of the optical disc, the scratch having the depth of 2 μm is defined as an absolute reference value for determining whether the quality of optical disc is good or poor. By testing the mechanical endurance of the surface of the optical disc, it is possible to quantize the generation degree of the scratch.

Figure 7:
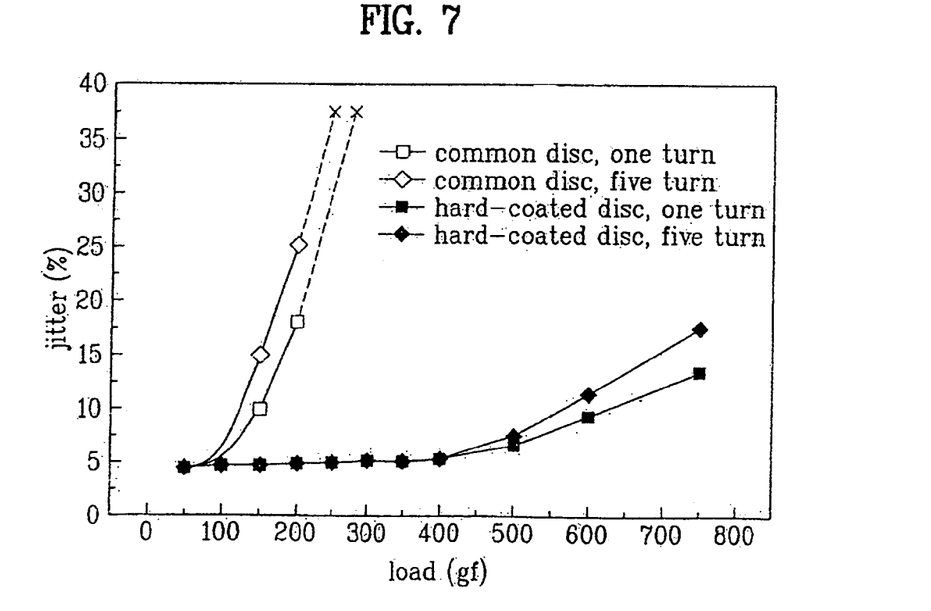
FIG. 7 illustrates a graph showing a change of jitter values depending on a load of an abrasion wheel applied on optical disc according to the present invention.

FIG. 7 illustrates a graph showing a change of jitter values depending on a load of an abrasion wheel applied on optical disc according to the present invention.

In FIG. 7, when the bare disc having no coating layer and the hard-coated disc having the coating layer are used, each of the bare disc and the hard-coated disc rotates by one turn and five turns, and the abrasion wheel of CS-10F is used.

As shown in FIG. 7, since the servo error having the jitter value above 10% or more generates, when the load is measured at a range between 50 gf and 750 gf, the load is preferable at a range between 250 gf and 500 gf below the jitter value of 10%.

Accordingly, in case of using the hard-coated disc, the load generated from the abrasion wheel is quantized to 50 gf to 750 gf, and is differently set according to the kind of abrasion wheels.

That is, in the taber abrasion test, under the condition of using the abrasion wheel of CS-10F, the optical disc rotates below ten turns, and the load is controlled at a range of approx. 50 gf to 250 gf.

In case of using the abrasion wheel of CS-10, the optical disc rotates below ten turns, and the load is controlled at a range of approx. 150 gf to 450 gf.

Also, under the condition of using the abrasion wheel of CS-17, the optical disc rotates below ten turns, and the load is controlled at a range of approx. 250 gf to 750 gf.

Therefore, in all cases from the soft abrasion wheel of CS-10F to the hard abrasion wheel of CS-17, the load of the surface of the optical disc is quantized between 50 gf and 750 gf.

Accordingly, the rotation number of the optical disc is decreased below ten turns, thereby reducing the abrasion degree of the optical disc by the abrasion wheel at minimum. As a result, it is possible to generate the scratch having a type that is very similar to that of the scratch generated in a real life, thereby enhancing the reliability in testing the mechanical endurance of the surface of the optical disc.

In other words, the scratch on the optical disc in the real life is generated by being scratched few times, on the contrary, the more times the abrasion wheels are scratched, the more the scratch during several rotation of the optical disc by using the taber abrasion tester makes a difference from the scratch in real life due to abrasion of ambient optical disc to be scratched.

In this reason, there is a problem in the reliability for the mechanical endurance test of the surface of the optical disc due to the scratch, and then this is the worst serious problem occurring in the mechanical endurance test of the surface of the optical disc according to the conventional art.

According to the present invention, since the number of turns of the optical disc can be reduced to one turn at minimum to ten turns at maximum value by the quantized-absolute reference value, the reliability of the mechanical endurance test of the surface of the optical disc can be enhanced by causing the scratch of type the closest the scratch in the real life.

Also, it is possible to test the endurance of the surface of the optical disc by generating the scratch on the surface of the optical disc through one turn of the optical disc at minimum. As a result, it is determined whether the quality of optical disc is good or poor with easiness and precision.

Furthermore, the mechanical characteristics of the surface of the optical disc may be quantized to the BD-RE available for the repetitive record reproduction, and the BD-WO available for one record reproduction.

Meanwhile, the apparatus and method for testing the mechanical endurance of the surface of the optical disc according to the present invention extracts a predetermined number of optical discs among the manufactured optical discs, and performs the test for the mechanical endurance with the extracted discs. If the discs have the endurance according to the present invention, it is assumed that other discs, not extracted for the test, also have the mechanical endurance, that is, the scratch endurance.

As mentioned above, the apparatus and method for testing the mechanical endurance of the surface of the optical disc according to the present invention have the following advantages.

First, the generation degree of the scratch is quantized to enhance the mechanical characteristics of the surface so that the preservation of data according to achievement for the high-density of the optical disc can be increased.

Second, since the quality of the optical disc is tested easily and precisely, the reliability of the optical disc can be enhanced.

Third, the scratch can be formed as much as to wish in a short time so that the testing time for the mechanical endurance test of the surface of the optical disc can be also decreased and the manufacturing cost may be reduced.

Fourth, the method for testing the mechanical endurance according to the present invention may be applied to the BD-RE available for the repetitive record reproduction, and the BD-WO available for one record reproduction, with satisfaction.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An apparatus for testing whether an optical disc is acceptable or not for scratch endurance on a surface of the optical disc, the apparatus comprising:
   a rotating plate configured to rotate the optical disc; and
   two abrasion wheels configured to begin the test by generating a scratch on the surface of the optical disc by applying a load to each wheel on the optical disc with 2.5N, and to record information on the scratched optical disc after beginning the test, the two abrasion wheels being further configured to determine whether the optical disc has a sufficient endurance by comparing a jitter value measured from a signal of reproducing information recorded on the scratched optical disc with a predetermined reference jitter value,
   wherein the two abrasion wheels are configured to rotate in an opposite direction with each other from a view point of one of the two abrasion wheels.

2. The apparatus according to claim 1, wherein at least one of the two abrasion wheels is of type CS-10F.

3. The apparatus according to claim 1, wherein the two abrasion wheels generate the scratch on the surface of the optical disc while the optical disc rotates five turns.

4. The apparatus according to claim 1, wherein the predetermined reference jitter value is 10%.

5. A method for testing whether an optical disc is acceptable or not for scratch endurance on a surface of the optical disc, comprising:
   contacting two abrasion wheels with a load to each wheel on the surface of the optical disc;
   maintaining the contact between the optical disc and the abrasion wheels to generate a scratch on the surface of the optical disc;
   recording information on the scratched optical disc;
   measuring a jitter value from a signal by reproducing the information; and
   determining whether the optical disc is acceptable or not by comparing the measured jitter value with a predetermined reference jitter value,
   wherein the two abrasion wheels rotate in an opposite direction with each other from a view point of one of the abrasion wheels.

6. The method according to claim 5, wherein at least one of the two abrasion wheels is of type CS-10F.

7. The method according to claim 5, wherein it is determined that the optical disc has a sufficient endurance if the jitter value is smaller than the predetermined reference jitter value.

8. The method according to claim 5, wherein the two abrasion wheels are contacted with a load of 2.5N to each wheel on the surface of the optical disc.

9. The method according to claim 5, wherein the scratch on the surface of the optical disc is generated while the optical disc rotates five turns.

10. The method according to claim 5, wherein the predetermined reference jitter value is 10%.

11. An apparatus for testing at least one optical disc, from among multiple discs of a same kind as the optical disc, to determine whether the optical disc is acceptable or not for scratch endurance on a surface of the optical disc, the apparatus comprising:
    a rotating plate configured to rotate the optical disc; and
    two abrasion wheels configured to begin the test by rotating in the opposite direction with each other from a viewpoint of one of the two abrasion wheels, and generating a scratch on the surface of the optical disc by applying a load to each wheel on the optical disc with 2.5N, the two abrasion wheels being further configured to record information on the scratched optical disc after beginning the test, and to determine whether the optical disc has a sufficient endurance by comparing a jitter value measured from a signal of reproducing information recorded on the scratched optical disc with a predetermined reference jitter value,
    wherein the apparatus is configured to determine the optical disc to be acceptable if the obtained jitter value is not greater than the predetermined reference jitter value.

12. The apparatus according to claim 11, wherein at least one of the two abrasion wheels is of type CS-10F.

13. The apparatus according to claim 11, wherein the two abrasion wheels generate the scratch on the surface of the optical disc while the optical disc rotates five turns.

14. The apparatus according to claim 11, wherein the predetermined reference jitter value is 10%.

15. A method for testing at least one optical disc, from among multiple discs of a same kind as the optical disc, to determine whether the optical disc is acceptable or not for scratch endurance on a surface of the optical disc, the method comprising:
    contacting two abrasion wheels rotating in the opposite direction with each other from a viewpoint of one of the abrasion wheels, with a load to the surface of the optical disc;
    maintaining the contact between the optical disc and the abrasion wheels to generate a scratch on the surface of the optical disc;
    recording information on the scratched optical disc;

measuring a jitter value from a signal by reproducing the information; and determining whether the optical disc is acceptable or not by comparing the measured jitter value with a predetermined reference jitter value, wherein the optical disc is determined to be acceptable if the measured jitter value is not greater than the predetermined reference jitter value.

16. The method according to claim 15, wherein the two of abrasion wheels are contacted with a load of 2.5N to each wheel on the surface of the optical disc.

17. The method according to claim 15, wherein the scratch on the surface of the optical disc is generated while the optical disc rotates five turns.

18. The method according to claim 15, wherein the predetermined reference jitter value is 10%.

19. The method according to claim 15, wherein at least one of the two abrasion wheels is of type CS-10F.

* * * * *

UNITED STATES PATENT AND TRADEMARK OFFICE
CERTIFICATE OF CORRECTION

PATENT NO. : 7,864,643 B2 Page 1 of 1
APPLICATION NO. : 11/520629
DATED : January 4, 2011
INVENTOR(S) : Hun Seo et al.

It is certified that error appears in the above-identified patent and that said Letters Patent is hereby corrected as shown below:

Title Page

Page 1, Number (30), Foreign Application Priority Data, line 2, reads:

Sep. 15, 2003 (KR)    10-2003-0064034

Page 1, Number (30), Foreign Application Priority Data, line 2, should read:

Sep. 16, 2003 (KR)    10-2003-0064034

Signed and Sealed this
Twentieth Day of September, 2011

David J. Kappos
*Director of the United States Patent and Trademark Office*